(12) United States Patent
Takahata et al.

(10) Patent No.: US 6,713,093 B2
(45) Date of Patent: Mar. 30, 2004

(54) ANTIALOPECIA AGENT

(75) Inventors: Kyoya Takahata, Okayama-ken (JP); Yokichi Matsui, Osaka (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/118,076

(22) Filed: Apr. 9, 2002

(65) Prior Publication Data

US 2002/0160058 A1 Oct. 31, 2002

Related U.S. Application Data

(63) Continuation of application No. 09/541,913, filed on Apr. 3, 2000, which is a continuation of application No. 09/260,146, filed on Mar. 1, 1999, now abandoned, which is a continuation of application No. 08/822,153, filed on Mar. 17, 1997, now abandoned.

(30) Foreign Application Priority Data

Mar. 18, 1996 (JP) ................................................ 7-61186
Mar. 13, 1997 (JP) ................................................ 8-59494

(51) Int. Cl.[7] ......................... A01N 65/00; A61K 35/78; A61K 47/00; A23L 1/28
(52) U.S. Cl. ...................... 424/729; 424/439; 426/597; 426/655
(58) Field of Search ............... 424/439, 729; 426/597, 655

(56) References Cited

U.S. PATENT DOCUMENTS

| 4,717,579 A | 1/1988 | Vietti ........................ 426/597 |
| 5,538,750 A | 7/1996 | Yamaguchi ................ 426/594 |
| 5,605,929 A | 2/1997 | Liao et al. .................. 514/456 |

FOREIGN PATENT DOCUMENTS

| JP | 03109313 | 5/1991 |
| WO | WO 96 37201 | 11/1996 |

OTHER PUBLICATIONS

Derwent Abstract FR 3203, published 1968, assigned to Kleinwichs.*
Hoffman, David, The Complete Illustrated Herbal, Barnes & Noble Books, New York, pp. 22 and 28 (1996).
John, D. "One Hundred Useful Raw Drugs of the Kani Tribes of Source". Int. J. Crude Drug Res (1984) 22(1) p. 17–39.*
Umeki et al. Anticancer Chemotherapy Accelerates Scalp Hair Loss with no Andorgenic Involvement Chemotherapy, vol. 35, pp. 54–57, 1989.
"Effects of Oolong Tea on Living Body" from Kohi to Ocha no Genkyo to Tenbo (The Present State and Prospects of Coffe and Tea, Aug. 31, 1989, pp. 208–223, Kogyo Gijutsu–kai.).
DATABASE WPI, Week 9125, Derwent Publications Ltd., XP–002089133, Abstract, JP 03109313, May 9, 1991.
DATABASE WPI, Week 9411, Derwent Publications Ltd., XP–002089134, Abstract, JP 06040860, Feb. 15, 1994.
Patent Abstracts of Japan, vol. 010, No. 328, JP 61 137809, Jun. 25, 1986.
Shigenobu Uemki et al., "Anticancer Chemotherapy Accelerates Scalp Hair Loss With No Androgenic Involvement", Chemotherapy, 1989, vol. 35, pp. 54–57.

* cited by examiner

*Primary Examiner*—Sreeni Padmanabhan
*Assistant Examiner*—Lauren Q. Wells
(74) *Attorney, Agent, or Firm*—Paul E. White, Jr.; Manelli Denison & Selter PLLC

(57) ABSTRACT

The present invention provides an antialopecia agent which is a drug for protecting, reducing or preventing alopecia frequently occurring as the side effect of anticancer agents, wherein the drug inflicts neither any pain nor unpleasantness on patients under the treatment with anticancer agents and has a high safety; and foods or beverages containing this antialopecia agent. The antialopecia agent of the present invention is characterized by containing oolong tea extract as the active ingredient.

4 Claims, No Drawings

ANTIALOPECIA AGENT

This is a continuation of Application No. 09/541,913 filed Apr. 3, 2000, which is a continuation of 09/260,146 filed Mar. 1, 1999 now abandoned which is a continuation of 08/822,153 filed Mar. 17, 1997, all now abandoned.

BACKGROUND OF THE INVENTION

This invention relates to a agent capable of protecting, reducting or preventing alopecia which frequently occurs as the side effect of anticancer agents. More particularly, it relates to an antialopecia agent characterized by containing oolong tea extract as the active ingredient.

A case of cancer has been on the remarkable increase, various anticancer agents have been developed and the new developed anticancer agents administered to the patients. On the other hand, there arises a serious problem of alopecia as the side effect of these anticancer agents. The alopecia occurring as the side effect of anticancer agents rarely causes the discontinuance or alleviation of the dosing schedule of the anticancer agents, since the administration of the anticancer agents affect life and death for the patients, while the alopecia is no fatal side effect. However, alopecia occurs at a high incidence and ranks high as painful side effects, following vomiting and nausea, on patients under the treatment with anticancer agents. Also, there is no doubt about that patients with alopecia have perturbation and uneasiness. Namely, alopecia causes serious mental anguish.

Human hair grows through the differentiation of hair-matrix cells in hair follicles distributed in the whole body. It is known that hair follicles on the head (i.e., scalp hair organs) have the highest growth rate and the longest growth period and involve those in the growth stage at a high ratio, which makes the hair on the head the longest among all. From a clinical viewpoint, alopecia can be roughly classified into male pattern baldness, alopecia areata, alopecia senilis, alopecia congenitalis, alopecia accompanying dysbolism (for example, endocrinopathy), trophopathy, shock or systemic diseases (for example, prolonged high fever), secondary alopecia following various cutaneous disease on the scalp, and drug-induced alopecia. That is to say, the head hair follicles (scalp hair organs) are damaged by various factors including hereditary ones and diseases. Although the mechanism of alopecia induced by anticancer agents has not been fully clarified so far, it seemingly proceeds as follows. Because of having much higher biological activities than other hair organs, the scalp hair organs are liable to be damaged by anticancer agents similar to bone marrow lymphoid tissues and digestive tract mucosal epithelial tissues. Thus the hair-matrix cells in the hair follicles are damaged. As a result, the growth of the functions of the hair-matrix cell is ceased and hair bulbs are deformed. Thus the hair becomes atrophic or poor and falls off. Alternatively, the hair organs rapidly rush into the resting phase and thus the hair falls off.

Among anticancer agents, anthracycline derivatives typified by adriamycin, endoxan (cyclophosphamide) and etoposide induce severe alopecia at a high frequency. In addition, alopecia is induced by nitrosourea, 5-fluorouracil, cisplatin, interferon, etc. It is pointed out in many papers that adriamycin or etoposide causes alopecia at a ratio of 60 to 80%. It is further pointed out that the administration of each anticancer agent in a higher single dose results in the higher incidence of alopecia.

To cope with the alopecia occurring as the side effect of anticancer agents, attempts have been made to administer an anticancer agents together with an antagonist (for example, Co-enzyme $Q_{10}$) specific thereto; to select an administration route other than oral or intravenous administration so as to reduce the amount of an anticancer agents reaching the scalp hair organs (for example, intraarterial or intraperitoneal administration); or to reduce the blood flowing into the scalp with the use of avascularization belts to thereby inhibit the access of an anticancer agents to hair roots (i.e., the scalp blood stream blocking method). However, none of these method can achieve any satisfactory effect. In the case of the selection of the administration route, for example, intraarterial administration is usable only in cancers being under arterial control definitely (for example, liver tumors), which restricts the application range thereof. On the other hand, the scalp blood stream blocking method suffers from a problem that it causes intense pain. Another method for inhibiting alopecia comprises regulating the scalp temperature to 22° C. or below, i.e., the skull (head) cooling method. However the evaluation of the efficacy of this method is divided into two. It is reported that this method exerts no effect, in particular, when an anticancer agents is used in an increased dose or administered orally. Moreover, this method has disadvantageous in that the prolonged cooling period demands that the patient could not move for long time and the appearance makes the patient unpleasant. In addition, troublesome nursing care is also needed therefor. Other known methods for coping with alopecia are limited to preventive means such as the application of hair growth creams (for example, hair nourishing protein creams) not stimulating the scalp and having no vasodilator effect, keeping the head clean, maintaining the whole body in a good nutritional status, easy mental state, etc. Anyway, no remarkable and fundamental means has been established therefor hitherto.

There has been reported nothing but the oral administration of tocopherol as a means for preventing drug-induced alopecia via the administration of medicines. It is reported that the oral administration of tocopherol exerts a preventive effect on alopecia induced by adriamycin. However, it is also reported that tocopherol exerts no effect on alopecia induced by the combined use of adriamycin with other anticancer agents. In the alopecia induced by the administration of anticancer agents, hair-matrix cells are not completely broken. Namely, it is a temporary or reversible symptom. In recent years, therefore, a number of patients suffering from alopecia wear wigs for medical use until the effect of the anticancer agents disappears and hair newly grows after the termination of the administration of anticancer agents.

Accordingly, it has been urgently desired to develop a safe and efficacious antialopecia agent which inflicts neither any pain nor unpleasantness on patients under the administration of anticancer agents and has no side effects.

SUMMARY OF THE INVENTION

To develop a agent for alopecia caused by anticancer agents, the present inventors have examined a number of substances and conducted extensive studies. As a result, they have successfully found out that the application of oolong tea extract can achieve an effect of protecting, reducing or preventing alopecia. The present invention has been completed based on this new finding. Moreover, the present inventors have confirmed that the oolong tea extract is also efficacious against alopecia caused by the cessation of the growth of the hair-matrix cell function or by the resting phase of the hair-matrix cell induced by anticancer agents. Thus, it is also efficacious against alopecia caused by a number of other factors.

Accordingly, the present invention provides an antialopecia agent characterized by containing oolong tea extract as the active ingredient.

The present invention further provides a foods or beverages containing the above-mentioned antialopecia agent.

DETAILED DESCRIPTION

Oolong tea is a semi-fermented tea originating in China. It has been widely taken in China from ancient times. With the spread of Chinese dishes, it is now taken all over the world. In these days, there are a number of oolong tea-lovers in Japan too. Because of being a tea beverage, it is taken in a large amount everyday for a long time. Nevertheless, no harmful effect of oolong tea has been found out so far. On the contrary, animal experiments with the use of rats and rabbits indicate that the continuous intake of oolong tea for a long time causes no problem in safety. That is to say, oolong tea is a highly safe beverage and, therefore, can be given to human with a high safety. From the standpoint of patients, oolong tea, which is familiar as an everyday beverage, can be pleasantly and positively taken without any discomfort or anxiety.

The oolong tea extract to be used in the present invention can be obtained by extracting oolong tea leaves with water heated to from room temperature to 100° C. The extraction time ranges from 10 seconds to 24 hours, though it varies depending on the temperature of the water and the desired concentration of the extract. The water to be used in the extraction may contain an alcohol, preferably ethanol. It is sometimes observed that sodium hydrogen carbonate is added to the water by which oolong tea leaves are extracted or sodium hydrogen carbonate, sodium L-ascorbate, etc. are added to the extract to thereby improve its preference, etc. Since these additives have no undesirable effect, the products thus obtained are also usable as the oolong tea extract in the present invention.

The oolong tea extract of the present invention is the one which is obtained by extracting oolong tea leaves with heated water and has a concentration ranging from 0.1 to 30% by weight (Brix; the content of solid matters). Oolong tea usually taken as beverages has a concentration of from 0.1 to 1% by weight. It is therefore preferable from the viewpoint of preference that the oolong tea extract has a concentration falling within the above range, since it can be drunk as such. When the oolong tea extract has a concentration higher than the range usually employed as beverages, it sometimes tastes bitter when drunk as such. In this case, it may be taken preferably in the form of a thickened extract, a freeze-dried powder, etc. optionally processed into tablets, capsules, etc. When the oolong tea extract has a concentration lower than the range usually employed as beverages, it can be drunk as such. In this case, however, it is often undesirable from the viewpoint of preference. To achieve the desired concentration, the extract can be appropriately diluted with water or concentrated by, for example, evaporation before using.

The oolong tea extract provided by the present invention can be orally administered either as such (i.e., in the form of the extract) or after diluting with water. Alternatively, the extract may be formulated into liquid preparations for oral use such as syrups. Furthermore, it may be formulated into a thickened extract, a powder, etc. and blended with pharmaceutically acceptable carriers to thereby give solid preparations for oral use such as tablets, capsules, granules, powders, etc. As the pharmaceutically acceptable carriers, use can be made of various organic and inorganic materials commonly employed in the art as carriers. For example, fillers, lubricants, binders, disintegrator, etc. may be used in solid preparations, while solvents, fillers, suspending agents, binders, etc. may be used in liquid preparations. Furthermore, use can be made of various additives such as preservatives, antioxidants, coloring agents and sweeteners, if necessary.

Appropriate examples of the fillers include lactose, sucrose, D-mannitol, starch, crystalline cellulose and light anhydrous silicic acid. Appropriate examples of the lubricants include magnesium stearate, calcium stearate, talc and colloidal silica. Appropriate examples of the binders include bound cellulose, sucrose, D-mannitol, dextrin, hydroxypropylcellulose, hydroxypropylmethylcellulose and polyvinyl pyrrolidone. Appropriate examples of the disintegrators include polyethylene glycol, propylene glycol, D-mannitol, benzyl benzoate, ethanol, trisaminomethane, cholesterol, triethanolamine, sodium carbonate and sodium citrate. Appropriate examples of the solvents include purified water, alcohols and propylene glycol. Appropriate examples of the suspending agents include ethanolamine stearate, sodium lauryl sulfate, laurylamino-6propionic acid, lecithin, benzalkonium chloride, benzethonium chloride, surfactants such as glycerol monostearate, and hydrophilic polymers such as polyvinyl alcohol, polyvinyl pyrrolidone, sodium carboxymethylcellulose, methylcellulose, hydroxymethylcellulose, hydroxyethylcellulose and hydroxypropylcellulose. Appropriate examples of the preservatives include parahydroxybenzoates, chlorobutanol, benzyl alcohol, phenethyl alcohol, dehydroacetic acid and sorbic acid. Appropriate examples of the antioxidants include sulfites and ascorbic acid.

The oolong tea extract provided by the present invention can be administered as such (i.e., as the extract). Alternatively, it may be formulated into a thickened extract, powder, etc. which is then processed into foods or beverages. It may be blended with edible materials commonly employed and carriers acceptable in manufacturing foods and beverages and then served as foods or beverages. Examples of the beverages include oolong tea beverages, tea beverages prepared by mixing with other tea, carbonated beveragges, fruit beverages, lactic acid beverages, sport beverages and soya milk. Examples of the confectionery include biscuits, chocolates, candies, chewing gums, snacks, fried cakes, fresh cakes, Japanese cakes, ice creams and jellies. Examples of the foods include breads, noodles, processed soybean products such as tofu (bean curd), dairy products such as yoghurt and butter, processed meat products such as ham and sausage, processed egg products such as tamago-yaki (Japanese omelet) and chawan-mushi (custard- like dish steamed in a cup), processed marine products such as tsukuda-ni (small fishes and shellfishes boiled in sweetened soy sauce), ground fish meat products such as kamaboko (boiled fish paste), seasonings such as sauce, dressing, mayonnaise and furikake (rice topping) and prepared dishes such as curry, stew, hamburg steak and soup. These products can be each produced in a conventional manner.

Examples of the carries acceptable in manufacturing foods and beverages include sweeteners such as sucrose, glucose, fructose, isomerized liquid sugars, fructoligosaccharide, aspartame, sorbitol and stevia; coloring agents such as red cabbage colorant, grape pericarp colorant, elderberry colorant, caramel, gardenia colorant, corn colorant, saffron colorant and carotene; preservatives such as pectin decomposition products, benzoic acid, sorbic acid, parabens and potassium sorbate; thickeners such as sodium alginate, propylene glycol alginate, calcium cellulose glycolate and sodium cellulose glycolate; antioxidants such as L-ascorbic acid, tocopherol, erythrobic acid and rutin; color developing agents such as ferrous sulfate, sodium nitrite and potassium nitrate; bleaching agents such as sodium hydrogen nitrite and potassium metabisulfite; quality keeping agents such as propylene glycol; quality improving agents such as L-cysteine hydrochloride and calcium stearyl lactate; inflating agents such as ammonium chloride, potassium hydrogen D-tartrate, ammonium carbonate, potassium carbonate, sodium hydrogen carbonate and alum; emulsifiers such as lecithin, sphingo-lipids, vegetable sterols, soybean saponin, sodium alginate, propylene glycol alginate, casein sodium, glycerol fatty acid esters, sucrose fatty acid esters and sorbitan fatty acid esters; emulsion stabilizers such as sodium chondroitin sulfate; flavoring substances such as lemon oil, eucalyptus oil, peppermint oil, vanilla extract, orange oil, garlic oil, ethyl acetoacetate, anisaldehyde, ethyl vanillin, cinnamic acid, citronellyl acetate, citral, vanillin, butyl butyrate and esters; mourishing agents such as L-ascorbic acid, L-asparagine, L-alanine, inositol, L-glutamine, carotene, tocopherol, vitamin A, folic acid, iron citrate, heme iron and uncalcined calcium; wheat flour-improving agents such as benzoyl peroxide, ammonium persulfate and chlorine dioxide; bactericides such as bleaching powder, hydrogen peroxide and hypochlorous acid; chewing gum bases such as methyl acetylricinolate, ester gum, vinyl acetate resin, polyisobutylene and polybutene; anti-blocking agents such as D-mannitol; integrating agents such as acidic sodium pyrophosphate, potassium pyrophosphate and sodium pyrophosphate; acidifiers such as adipic acid, citric acid, gluconic acid, succinic acid, D-tartaric acid, lactic acid and DL-malic acid; and seasonings such as fish extract, yeast extract, sea tangle extract, soy sauce, tomato puree, meat extract, mirin (sweetened sake for seasoning), fruit puree, dried bonito, sodium L-aspartate, DL-alanine, L-arginine L-glutamate, disodium 5'-inosinate, trisodium citrate, L-glutamic acid, sodium L-glutamate, succinic acid, L-tartaric acid and sodium lactate.

The dose of the oolong tea extract according to the present invention may widely vary depending on the severity of the alopecia, relative health status, age, sex, body weight, etc. of the subject to which it is administered. Usually, the daily dose of the oolong tea extract may range from 0.1 to 20 g (in terms of the solid matters) in the case of an adult weighing 60 kg. It may be administered once to several tens times per day. A daily dose thereof exceeding 20 g causes neither any problem in safety nor disorders.

As the results of Test Example 1 and Test Example 2 as will be given hereinafter show, the oolong tea extract has a preventive or reductive effect on alopecia induced by etoposide which is an anticancer agent causing severe alopecia at a very high incidence.

It is clarified by the following Test Examples that the oolong tea extract of the present invention has a preventive or reductive effect on alopecia occurring as the side effect of anticancer agents. Moreover, the oolong tea extract has a similar preventive or reductive effect on alopecia induced by other factors, since these symptoms are caused by damaged hair-matrix cells in hair follicles. In addition, the oolong tea extract of the present invention has a high safety and no side effect. Thus it can be administered to subjects without any anxiety. The oolong tea extract of the present invention is usable not only as a drug but also as foods or beverages.

EXAMPLES

To further illustrate the present invention in greater detail, and not by way of limitation, the following Test Examples and Examples will be given. It is to be understood that modifications may be made therein without departing from the scope of the present invention.

Test Example 1
Antialopecia Effect on Alopecia Induced by Etoposide 54 male SD rats (6-days-old, Clea Japan) were classified into the following 4 groups (a) to (d). Then the samples specified below were administered to the rats continuously for 5 days. The rats of the group (a) were divided into groups each having 7 or 8 rats, while the rats of the groups (b), (c) and (d) were caged respectively. Each cage was provided with a mother rat and the infant rats were allowed to take breast milk and water ad libitum. The mother rats were allowed to take a solid feed CE2 (manufactured by Clea Japan) and water ad libitum too.
Sample:
 (a) None (no administration).
 (b) Oolong tea extract:
   (orally)0.1 ml/a rat.
 (c) Oolong tea extract (upper layer of sludge):
   (orally) 0.1 ml/a rat.
 (d) None (control).

The oolong tea extract given to the group (b) was prepared in the following manner. 200 g of oolong tea leaves were extracted with 6,000 ml of purified water at 90° C. for 5 minutes. The extract was filtered through a 120-mesh wire screen to thereby eliminate the leaves. The filtrate was further centrifuged at 3,000 rpm and then cooled to room temperature and thus the desired product was obtained. This oolong tea extract was containing 0.9% (Brix) of the soluble solid matters.

The oolong tea extract (upper layer of sludge) given to the group (c) was prepared in the following manner. 300 g of oolong tea leaves were extracted with 3,500 ml of purified water at 60° C. for 10 minutes. The extract was filtered through a 80-mesh vibrating screen to thereby eliminate the leaves. The filtrate was further centrifuged at 5,500 rpm and then cooled to room temperature. The obtained extract containing 2.8% (Brix) of the soluble solid matters was subjected to vacuum film concentration at a temperature of 60° C. or below until the concentration of the soluble solid matters was lowered to about 16%. Next, the extract thus concentrated was maintained at 5° C. overnight. Then the precipitate was removed and thus the supernatant (i.e., the upper layer) was obtained. This obtained supernatant was containing 20% (Brix) of the soluble solid matters.

Since the day 11 after birth, 1.5 mg/kg of etoposide (VP-16; "Lastet" manufactured by Nippon Kayaku Co., Ltd.), which was employed as an anticancer agent inducing alopecia, was intraperitoneally injected into the rats of the groups (a), (b) and (c) daily for 3 days. To the group (d), physiological saline was intraperitoneally administered in the same dose as a substitute for etoposide. In each group, the administration was performed once a day between 10 to 11 a.m. On the day 20 after birth, the degrees of alopecia were evaluated with the naked eye. Table 1 shows the results. The degrees of alopecia were expressed in 4 grades (0 to 3) as shown below.
Criteria for the Evaluation of Alopecial
 0: alopecia observed at a ratio of 0 to 25%.
   (no detectable alopecia)
 1: alopecia observed at a ratio of 26 to 50%.
   (mild alopecia)
 2: alopecia observed at a ratio of 51 to 75%.
   (moderately severe alopecia)

3: alopecia observed at a ratio of 76 to 100%.
(severe and total alopecia)

TABLE 1

| Day of Evaluation (in Days after Birth) | Sample | Number of Rats | Degree of Alopenia | | | |
|---|---|---|---|---|---|---|
| | | | 0 | 1 | 2 | 3 |
| 20 | (a) (None) + Etoposide | 37 | 0 | 9 | 12 | 16 |
| 20 | (b) Oolong tea extract + Etoposide | 8 | 0 | 1 | 4 | 3 |
| 20 | (c) Oolong tea extract (upper layer of sludge) + Etoposide | 3 | 2 | 0 | 0 | 1 |
| 20 | (d) (None) + Physiological saline (Control) | 6 | 6 | 0 | 0 | 0 |

Test Example 2
Antialopecia Effect on Alopecia Induced by Etoposide 25 male SD rats (6-days-old, Clea Japan) were classified into the following 3 groups (a), (c) and (d). Then the samples specified below were administered to the rats continuously for 5 days. The rats of the group (a) were divided into groups each having 6 or 7 rats, the rats of the groups (b) were divided into groups each having 5 rats, and the rats of group (d) were caged respectively. Each cage was provided with a mother rat and the infant rats were allowed to take breast milk and water ad libitum. The mother rats were allowed to take a solid feed CE2 (manufactured by Clea Japan) and water ad libitum too.
Sample
  (a) None (no administration)
  (c) Oolong tea extract (upper layer of sludge):
     (orally) 0.1 ml/a rat
  (d) None (control)

The oolong tea extract (upper layer of sludge) given to the group (c) was prepared in the following manner. 300 g of oolong tea leaves were extracted with 3,500 ml of purified water at 60° C. for 10 minutes. The extract was filtered through a 80-mesh vibrating screen to thereby eliminate the leaves. The filtrate was further centrifuged at 5,500 rpm and then cooled to room temperature. The obtained extract containing 2.8% (Brix) of the soluble solid matters was subjected to vacuum film concentration at a temperature of 60° C. or below until the concentration of the soluble solid matters was lowered to about 16%. Next, the extract thus concentrated was maintained at 5° C. overnight. Then the precipitate was removed and thus the supernatant (i.e., the upper layer) was obtained. This obtained supernatant was containing 20% (Brix) of the soluble solid matters.

Since the day 11 after birth, 1.5 mg/kg of etoposide (VP-16; "Lastet" manufactured by Nippon Kayaku Co., Ltd.), was intraperitoneally injected into the rats of the groups (a) and (c) daily for 3 days. To the group (d), physiological saline was intraperitoneally administered in the same dose as a substitute for etopopside. In each group, the administration was performed once a day between 10 to 11 a.m. On the day 20 after birth, the degrees of alopecia were evaluated with the naked eye. Table 1 shows the results. The degrees of alopecia were expressed in 4 grades (0 to 3) as shown below.
Criteria for the Evaluation of Alopecia
  0: alopecia observed at a ratio of 0 to 25%.
     (no detectable alopecia)
  1: alopecia observed at a ratio of 26 to 50%
     (mild alopecia)
  2: alopecia observed at a ratio of 51 to 75%.
     (moderately severe alopecia)
  3: alopecia observed at a ratio of 76 to 100%.
     (severe and total alopecia)

TABLE 2

| Day of Evaluation (in Days after Birth) | Sample | Number of Rats | Degree of Alopenia | | | |
|---|---|---|---|---|---|---|
| | | | 0 | 1 | 2 | 3 |
| 20 | (a) (None) + Etoposide | 13 | 0 | 2 | 4 | 7 |
| 20 | (c) Oolong tea extract (upper layer of sludge) + Etoposide | 10 | 5 | 2 | 2 | 1 |
| 20 | (d) (None) + Physiological saline (Control) | 2 | 2 | 0 | 0 | 0 |

Example 1
Production of Oolong Tea Extract (Extract)

100 g of oolong tea leaves were poured into 5,000 ml of boiling purified water. After saturating the tea leaves with the water by stirring well, the mixture was maintained for 5 minutes at 90° C. or above. Then the tea leaves were separated from the extract by filtering through a cotton flannel filter to thereby give the oolong tea extract.

Example 2
Production of Oolong Tea Extract (Processed Extract)

500 g of oolong tea leaves were poured into 5,000 ml of a boiling solution prepared by mixing purified water with ethanol at a weight ratio of 2:1. After saturating the tea leaves with the solution by stirring well, the mixture was maintained for 30 minutes at 90° C. or above. Then the tea leaves were separated from the extract by filtering through a 100-mesh screen. Further, the filtrate was centrifuged at 3,000 rpm to thereby give 4,000 ml of an oolong tea extract. The obtained extract was kept overnight at 5° C. or below to thereby separate the supernatant from the precipitate. The concentration of the soluble solid matters in the supernatant was regulated to 15% (Brix) and then it was frozen at −40° C. followed by freeze-drying. thus an oolong tea extract powder was obtained.

Example 3
Production of Tablet

| | |
|---|---|
| Oolong tea extract powder (produced in Example 2) | 10 mg |
| lactose | 53 mg |
| corn starch | 16 mg |
| magnesium stearate | 1 mg |
| | 80 mg. |

The extract powder obtained in Example 2 was homogeneously mixed with lactose and corn starch. Then the obtained mixture was wet-granulated with the use of a corn starch binder. Further, magnesium stearate was added thereto and the resulting mixture was processed into tablets.

Example 4
Production of Oolong Tea Beverage 100 g of oolong tea leaves were poured into 1,000 ml of boiling purified water. After saturating the tea leaves with the water by stirring well, the mixture was maintained for 5 minutes at 90° C. or above. Then the tea leaves were separated from the extract by filtering successively through a 100-mesh wire screen and a cotton flannel filter to thereby give the oolong tea extract. The extract was cooled to 30° C. and then a small amount of ascorbic acid was added thereto. Then the mixture was heated to 90° C. and, in the hot state, packed into cans. After sealing and retorting at 120° C. for 15 minutes, it was cooled to room temperatures to thereby give an oolong tea beverage.

Example 5

Production of Jelly Containing Oolong Tea Extract

The following materials were employed for the production:

| oolong tea extract (produced in Example 2) | 2 g |
|---|---|
| sugar | 500 g |
| starch syrup | 500 g |
| pectin | 13 g |
| citric acid | 4 g |
| sodium citrate | 1.5 g |
| flavoring substance | 1 cc |
| edible colorant | 0.2 g |

13 g of pectin was mixed with 20 g of sugar and then the obtained mixture was dissolved in 330 cc of water with caution so as not to form undissolved portions. Further, citric acid and sodium citrate were added thereto and the resulting mixture was boiled. After adding starch syrup, the mixture was heated to 100° C. Then the residual sugar was added thereto and the mixture was heated to 109° C. After allowing to stand for several minutes, the oolong tea extract, flavoring substance and colorant were added. The obtained mixture was stirred and filled into a starch mold. Then it was dried at 50° C. or below for 10 hours or longer and thus a jelly containing the oolong tea extract was obtained.

Example 6

Production of Cookie Containing Oolong Tea Extract

The following materials were employed for the production:

| oolong tea extract (produced in Example 2) | 2 g |
|---|---|
| sugar | 430 g |
| weak wheat flour | 680 g |
| butter (salt-free) | 220 g |
| whole egg | 150 g |
| baking powder | 6 g |

Butter was softened and sugar was added thereto. The obtained mixture was vigorously stirred until it became creamy. Then whole egg was added thereto and the mixture was further stirred. Next, weak wheat flour and baking powder were added thereto and the mixture was lightly stirred crosswise. Finally, the oolong tea extract was added thereto. The mixture was squeezed out of a pastry bag onto an oven plate. After molding, it was baked in a pre-heated oven at 180° C. for 11 to 13 minutes to thereby give cookies containing the oolong tea extract.

Example 7

Production of Kamaboko Containing Oolong Tea Extract

The following materials were employed for the production:

| oolong tea extract (produced in Example 2) | 1 g |
|---|---|
| ground Alaska pollack meat | 100 g |
| sodium chloride | 20 g |
| seasoning | 2 g |
| egg white | 10 g |

Sodium chloride, seasoning, egg white and the oolong tea extract were added to the ground Alaska pollack meat. After kneading and maturing, the mixture was molded and steamed in a steamer pre-heated to about 90 to 95° C. Then it was cooled by allowing to stand to thereby give a kamaboko containing the oolong tea extract.

What is claimed is:

1. A method of treating alopecia, induced by anticancer agents selected from the group consisting of adriamycin, cyclophosphamide, etoposide, nitrosourea, 5-fluorouracil, cisplatin and interferon, which comprises orally administering to a person in need of such treatment, a pharmaceutically effective amount of anti-alopecia agent comprising an oolong tea extract as an active agent.

2. The method of claim 1, wherein the anti-alopecia agent is administered as a component of a food or beverage.

3. The method of claim 1, wherein the anti-alopecia agent is present in a composition that includes a pharmaceutically acceptable carrier.

4. The method of claim 1, wherein said pharmaceutically effective amount is from 1.6 mg to 333 mg tea extract per kg adult body weight.

* * * * *